US012636243B2

(12) United States Patent
Deshayes et al.

(10) Patent No.: US 12,636,243 B2
(45) Date of Patent: May 26, 2026

(54) INCREASED SOLUBILIZATION OF ISCOTRIZINOL

(71) Applicant: DSM IP ASSETS B.V., Heerlen (NL)

(72) Inventors: Cyrille Deshayes, Kaiseraugst (CH); Christine Mendrok-Edinger, Kaiseraugst (CH)

(73) Assignee: DSM IP ASSETS B.V., Maastricht (NL)

( * ) Notice: Subject to any disclaimer, the term of this patent is extended or adjusted under 35 U.S.C. 154(b) by 342 days.

(21) Appl. No.: 18/256,149

(22) PCT Filed: Dec. 8, 2021

(86) PCT No.: PCT/EP2021/084822

§ 371 (c)(1),
(2) Date: Jun. 6, 2023

(87) PCT Pub. No.: WO2022/122839

PCT Pub. Date: Jun. 16, 2022

(65) Prior Publication Data

US 2024/0041735 A1 Feb. 8, 2024

(30) Foreign Application Priority Data

Dec. 9, 2020 (EP) .................................... 20212796

(51) Int. Cl.

| | |
|---|---|
| ***A61K 8/49*** | (2006.01) |
| ***A61K 8/04*** | (2006.01) |
| ***A61K 8/06*** | (2006.01) |
| ***A61Q 17/04*** | (2006.01) |

(52) U.S. Cl.

CPC ............ *A61K 8/4966* (2013.01); *A61K 8/042* (2013.01); *A61K 8/06* (2013.01); *A61Q 17/04* (2013.01); *A61K 2800/20* (2013.01); *A61K 2800/74* (2013.01)

(58) Field of Classification Search

None

See application file for complete search history.

(56) References Cited

U.S. PATENT DOCUMENTS

| | | | | |
|---|---|---|---|---|
| 2014/0288167 A1 | 9/2014 | Scialdone | | |
| 2021/0177719 A1* | 6/2021 | Lorant | ................... | A61Q 17/04 |
| 2023/0310291 A1* | 10/2023 | Galle | ..................... | A61Q 19/08 424/59 |

FOREIGN PATENT DOCUMENTS

| | | |
|---|---|---|
| JP | 2009-256339 | 11/2009 |
| JP | 2009256339 A | 11/2009 |
| WO | 2017046177 A1 | 9/2016 |
| WO | 2016185046 | 11/2016 |
| WO | 2018109353 A1 | 6/2018 |
| WO | 2018109354 A1 | 6/2018 |
| WO | 2018172228 A1 | 9/2018 |
| WO | WO 2019/096958 | 5/2019 |

OTHER PUBLICATIONS

The First Office Action, CN Application No. 202180082156.7, Mar. 29, 2025.

Darl Kuhn, "Personal care compositions providing high UVA/UVB light protection and radical scavenging effect", ip.com, Prior Art Database, May 5, 2009, 122 pages.

International Search Report for PCT/EP2021/084822 mailed Mar. 21, 2022, 3 pages.

Written Opinion of the ISA for PCT/EP2021/084822 mailed Mar. 21, 2022, 6 pages.

* cited by examiner

*Primary Examiner* — Nannette Holloman

(74) *Attorney, Agent, or Firm* — NIXON & VANDERHYE P.C.

(57) ABSTRACT

The present invention relates to cosmetic composition comprising an ester of a fatty acid and dextrin, a mixture of branched and linear saturated C15-C19, wherein said mixture comprised primarily branched saturated C15-C19, and a UV-filter of the formula (I). This cosmetic composition allows a high amount of the UV-filter of the formula (I) to be solubilized which leads to compositions having a very high absorbance of harmful UV light, i.e. to compositions having a high Sun Protection Factor (SPF).

(I)

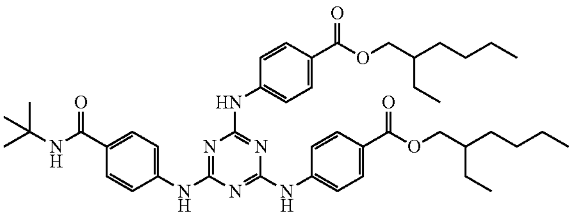

19 Claims, 1 Drawing Sheet

INCREASED SOLUBILIZATION OF ISCOTRIZINOL

CROSS-REFERENCE TO RELATED APPLICATIONS

This application is the U.S. national phase of International Application No. PCT/EP2021/084822 filed Dec. 8, 2021, which designated the U.S. and claims priority to EP 20212796.5 filed Dec. 9, 2020, the entire contents of each of which are hereby incorporated by reference.

TECHNICAL FIELD

The present invention relates to the field of cosmetic compositions which protect from UV light, particularly to cosmetic compositions comprising the UV-filter Iscotrizinol.

BACKGROUND OF THE INVENTION

Iscotrizinol is an highly effective UV(B) filter with an exceptional high absorptivity of the harmful UV light and is broadly used in cosmetic compositions. It has an outstanding photostability and moderate solubility particularly in esters and alcohols. However, the solubility in water and alkanes is very low.

It is important for the acceptance of a cosmetic composition that it has good sensory properties. Particularly the skin feeling is important. Products which result in a silky or velvet skin feeling on touch or fresh and gliding sensation with soft finish or comfortably afterfeel are significantly better accepted in the market.

Traditionally, silicone oils are used to improve the sensory properties in this direction. As the use of silicones oils in cosmetic products are getting more and more under pressure in the market particular for environmental and regulatory reasons, alternative substances leading to an increase of the sensory properties are highly searched.

It has been found that liquid C8-C30 alkanes can be used to improve the sensory properties and are suggested to be used for replacing silicone oils.

For example WO 2018/109353 A1 discloses a mixture of branched and linear saturated C15-C19 alkanes to improve the sensory properties of an oil-in-water emulsion.

A partial replacement of the solvent in cosmetic composition by such liquid alkanes with the goal to achieve improved sensory properties, however, reduces significantly the solubility of the UV filter Iscotrizinol, and, hence, leads to a strong reduction of the sun protection factor (SPF) of a respective cosmetic composition.

SUMMARY OF THE INVENTION

Therefore, the problem to be solved by the present invention is to obtain a high solubilization of the UV filter Iscotrizinol comprising liquid C8-C30 alkanes, particularly C15-C19 alkanes, in cosmetic compositions which have in particular improved sensory properties.

Surprisingly, it has been found that the cosmetic composition according to claim 1 allows to solve this problem.

It has been particularly found that this solution represent a highly sustainable and advantageous approach for this problem, as esters of fatty acids can be obtained from biological resources. This solution is even more attractive as also the preferred mixtures of C15-C19 alkanes can be obtained from biological origin. It is therefore, possible to offer cosmetic compositions having high sun protection factor (SPF) as well as excellent sensory properties.

Further aspects of the invention are subject of further independent claims. Particularly preferred embodiments are subject of dependent claims.

DETAILED DESCRIPTION OF THE INVENTION

Figure 1:
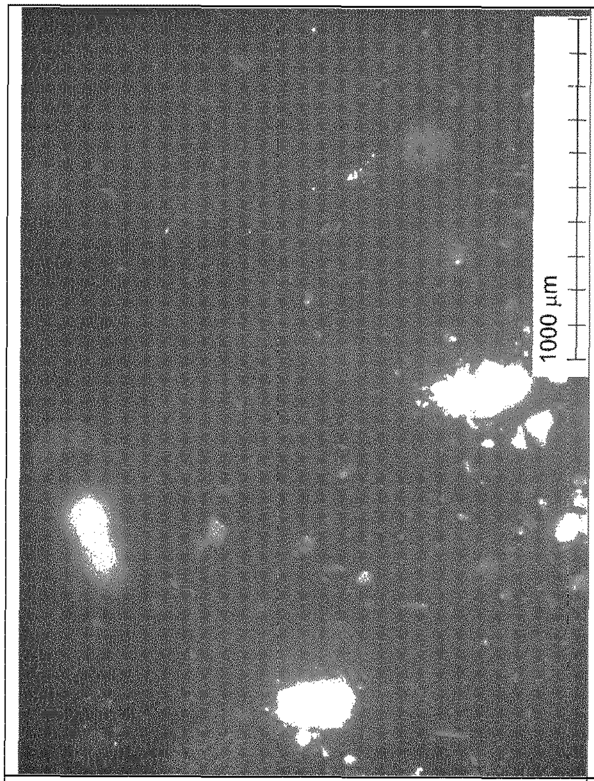
FIGS. 1-4 represent microscopic pictures (obtained with a Microscope Zeiss AX-10 under polarizer light, magnification X100, camera Deltapix Invenio 5D) of a composition according to Reference example 1 (Ref. 1), Reference example 2 (Ref. 2), Example 1 and Example 2, respectively, after one week of storage at 25° C.

In a first aspect the present invention relates to a cosmetic composition comprising

- an ester of a fatty acid and dextrin
- a mixture of branched and linear saturated C15-C19 alkanes
- a UV-filter of the formula (I)

(I)

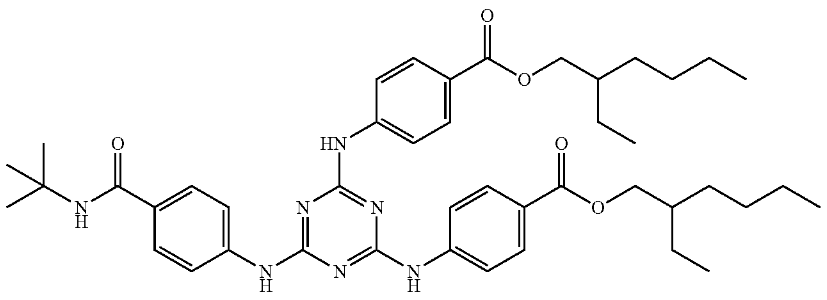

- wherein the amount of branched saturated C15-C19 alkane in said mixture of branched and linear saturated C15-C19 alkanes is more than 80% by weight, preferably more that 90% by weight, most preferred more than 92% by weight.

For sake of clarity, some terms used in the present document are defined as follows:

In the present document, a "$C_x$-$C_y$ alkane" is an alkane comprising x to y carbon atoms, i.e., for example, a C15-C19 alkane is an alkane comprising 15 to 19 carbon atoms. The alkane can be linear or branched (i.e. non-linear) and are purely saturated hydrocarbons. For example, all alkanes having the molecular formula $C_{15}H_{32}$, $C_{16}H_{34}$, $C_{17}H_{36}$, $C_{18}H_{38}$ and $C_{19}H_{40}$, such as pentadecane, octadecane, nonadecane, 2,6,10,14-tetramethylpentadecane, isohexadecane, are regarded as C15-C19 alkanes. Particularly preferred branched alkanes are branched alkanes having exclusively methyl group(s) as side chain(s), such as e.g. 2,6,10,14-tetramethylpentadecane, 2-methylpentadecane or 3-methylpentadecane.

In case identical labels for symbols or groups are present in several formulae, in the present document, the definition of said group or symbol made in the context of one specific formula applies also to other formulae which comprises the same said label.

The term "UV filter" in the present document stands for a substance that absorbs ultraviolet light (=UV light), i.e. electromagnetic radiation of the wavelength between 280 and 400 nm.

A liquid organic UV filter is liquid at ambient temperature (i.e. 25° C.).

A solid organic UV filter is solid at ambient temperature (i.e. 25° C.).

The term "solubilize" or "solubilization" in the present document describes the property that the UV filter of the formula (I) is incorporated in the cosmetic composition in such a manner that the UV-filter is not precipitated or separated at ambient temperature from the composition.

A "mixture of branched and linear saturated C15-C19 alkanes" in the present document means that said mixture comprises different alkanes each of them only having 15, 16, 17, 18 or 19 carbon atoms but does not comprise any alkanes having less carbons. Therefore, such a mixture does not contain for example dodecane or isododecane. Said mixture comprises both branched and linear C15-C19 alkanes.

UV Filter of Formula (I)

The cosmetic composition comprises the UV-filter of the formula (I)

Dextrin is an oligomer polymers of D-glucose. Its structure can be represented simplified by the following structure

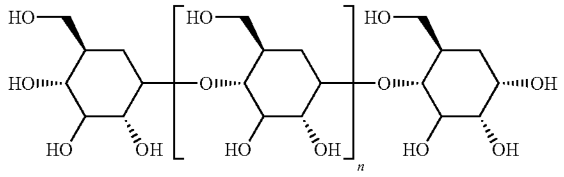

Dextrins have different average degrees of glycopolymerization which leads to different molecular weights.

In the present invention, the dextrin of said ester of a fatty acid and dextrin has preferably an average degree of glycopolymerization of between 3 and 20, particularly between 8 and 16.

It is preferred that the fatty acid of said ester of a fatty acid and dextrin is a C14-C18 fatty acid, particularly a linear C14-C18 fatty acid, most preferably palmitic acid.

As particular suitable ester of a fatty acid and dextrin is a dextrin palmitate as commercialized as Rheopearl® KL2 by Chiba Flour Milling.

Dextrin has several hydroxyl groups which can be esterified.

It is preferred that said ester of a fatty acid and dextrin has an average number of esterified hydroxyl groups of more than 2.5, preferably between 2.7 and 3.5, more preferably between 28 and 3.4, most preferably between 2.8 and 3.2, per glucose unit.

In one embodiment said ester of a fatty acid and dextrin has an average number of esterified hydroxyl groups of more than 3, preferably between 3.05 and 3.5, more preferably between 3.1 and 3.4, most preferably between 3.1 and 3.2, per glucose unit.

(I)

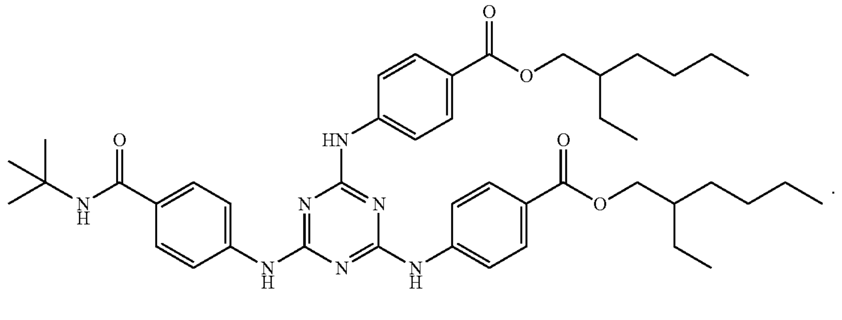

The UV-filter of the formula (I) (CAS: [154702-15-5]) is a light yellow crystalline solid with a melting point of 52-55° C. and is also known as Iscotrizinol or diethylhexyl butamido triazone (INCI). The UV filter is a highly effective UV(A) and UV(B) filter with an exceptional high absorptivity and is very highly photostable.

It has an absorption maximum of about 310 nm. It is commercially available for example under the trademark UVASORB® HEB from 3V Sigma.

Due to its polarity, it is very soluble in esters, and alcohols, particularly in ethanol, however, is insoluble in water and alkanes.

Ester of a Fatty Acid and Dextrin

The cosmetic composition further comprises an ester of a fatty acid and dextrin.

In other words, preferably essentially all of the hydroxyl groups of the dextrin are esterified.

It is further preferred that said ester of a fatty acid and dextrin has an molecular weight $M_n$ of between 8,000 and 16,000 Da, preferably between 9,000 and 13,000 Da, more preferably between 10,000 and 11'500 Da.

The molecular weight $M_n$ is determined in Dalton (Da) particularly by SEC/GPC using polystyrene as standard.

Both fatty acid and dextrin have biological origin. The biological origin of chemicals is very advantageous as such material or products thereof have a high degree of sustainability. High sustainable products or compositions are highly demanded in the market.

Mixture of Branched and Linear Saturated C15-C19 Alkanes

The cosmetic composition comprises a mixture of branched and linear saturated C15-C19 alkanes.

Particular suitable mixtures of C15-C19 alkanes are particularly the ones disclosed in WO 2016/185046, WO 2017/046177, WO 2018/109353 A1 and WO 2018/109354 A1 and WO 2018/172228 A1.

Preferably, the mixture of branched and linear saturated C15-C19 alkanes has a content of carbon of biological origin being greater or equal to 90% with respect of the total weight of the mixture of branched and linear saturated C15-C19 alkanes. The biological origin of chemicals is very advantageous as such material has a high degree of sustainability. High sustainable products or compositions are highly demanded in the market.

The determination of the content of biomaterial or content of biocarbon is given pursuant to standards ASTM D 6866-12, method B (ASTM D 6866-06) and ASTM D 7026 (ASTM D 7 026-04). Standard ASTM D 6866 concerns "Determining the Biobased Content of Natural Range Materials Using Radiocarbon and Isotope Ratio Mass Spectrometry Analysis", while standard ASTM D 7 026 concerns "Sampling and Reporting of Results for Determination of Biobased Content of Materials via Carbon Isotope Analysis". The second standard mentions the first in its first paragraph. The first standard describes a test of measurement of the ratio $^{14}C/^{12}C$ of a sample and compares it with the ratio $^{14}C/^{12}C$ of a sample renewable reference of origin 100%, to give a relative percentage of C of origin renewable in the sample. The standard is based on the same concepts that the dating with $^{14}C$.

It is further preferred that the composition has no or a very small amount (less than 100 ppm, particularly less than 30 ppm) of aromatic hydrocarbons with respect to the total weight of the mixture of branched and linear saturated C15-C19 alkanes.

The mixture of branched and linear saturated C15-C19 alkanes is particularly produced by catalytic hydrogenation of hydrocarbon biomass feedstock, such as described in detail in WO 2016/185046, particular the one disclosed as example 3 of WO 2016/185046.

It is preferred that the amount of linear saturated C15-C19 alkanes in said mixture of branched and linear saturated C15-C19 alkanes is less than 10% by weight, preferably less than 8% by weight, most preferred more than 5% by weight.

It is further preferred that the amount of C15 is less than 3%, particularly less than 1%, preferably less than 0.05%, by weight in respect to the weight of said mixture of branched and linear saturated C15-C19 alkanes.

It is preferred that the mixture of branched and linear saturated C15-C19 alkanes is a mixture of branched and linear saturated C16-C19 alkanes.

It is further preferred that the amount of branched saturated C16-C18 alkane is more than 90% by weight, preferably more than 95% by weight in respect to the weight of said mixture of branched and linear saturated C15-C19 alkanes.

It is further preferred that the amount of C15 alkanes is less than 5%, particularly less than 2%, by weight in respect to the weight of said mixture of branched and linear saturated C15-C19 alkanes.

It is further preferred that the amount of branched saturated C17-C18 alkane is more than 85% by weight, preferably more than 92% by weight in respect to the weight of said mixture of branched and linear saturated C15-C19 alkanes.

It is further preferred that the amount of C17 alkanes is more between 15 and 20% by weight in respect to the weight of said mixture of branched and linear saturated C15-C19 alkanes.

It is further preferred that amount of branched saturated C18 alkane is more than 50% by weight, preferably more than 60% by weight, even more preferably more than 70% by weight, relative to the weight of said mixture of branched and linear saturated C15-C19 alkanes.

It is further preferred that the amount of C18 alkanes is particularly between 70 and 75% by weight in respect to the weight of said mixture of branched and linear saturated C15-C19 alkanes.

In other words, the mixture of branched and linear saturated C15-C19 alkanes consist preferably mainly of C18 alkane(s), most preferably mainly of branched C18 alkane (s).

As the cosmetic composition comprises a mixture of branched and linear saturated C15-C19 alkanes, said composition does not comprise any lower alkanes, i.e. it does particularly not comprise any C12 alkanes and particularly does not comprise any C12 or C13 or C14 alkanes.

It is further preferred that the mixture of C15-C19 alkanes has at 20° C., a viscosity of 3-15 mPa·s, particularly between 6 and 12 mPa·s.

It is further preferred that the mixture of C15-C19 alkanes has at 20° C. a refractive index of between 1.40 and 1.48, particularly of between 1.42 and 1.45, most preferably between 1.43 and 1.44.

It is further preferred that the mixture of C15-C19 alkanes is the mixtures of C15-C19 alkanes as commercialized as EMOGREEN™ L19 by SEPPIC.

In the said composition the ratio of the weight of said ester of a fatty acid and dextrin to the weight of said mixture of branched and linear saturated C15-C19 alkanes is preferably less than 100% by weight, preferably in the range of 50-80% by weight, most preferred in the range of 60-70% by weight.

In other words, the composition comprises preferably more, by weight, of the C15-C19 alkanes than of the ester of a fatty acid and dextrin.

Furthermore, in said composition the weight ratio of the UV-filter of the formula (I) to the ester of a fatty acid and dextrin is preferably is 100:1 to 1:100, preferably 80:1 to 1:100, more preferably 70:1 to 1:20, most preferably 60:1 to 1:10.

Furthermore, it is preferred that said composition is in the form of a gel.

It is preferred that the cosmetic composition has a viscosity, measured on a Rheometer AR550 from TA Instruments using a 40 mm plate and a shear 10/s at 25° C., of more than 1,000 mPa·s, preferably more than 2,000 m Pas. It is further preferred that said viscosity is less than 100,000 mPa·s, preferably less than 50,000 mPa·s, more preferred less than 40,000 mPa·s.

Said composition has preferably a Sun Protection Factor (SPF) of 10 or higher, preferably of 20 or higher, more preferred of 30 or higher, even more preferred 50 or higher.

It is preferred that the mixture of branched and linear saturated C15-C19 alkanes and the a fatty acid and dextrin are both based on organic origin.

It is furthermore preferred that the mixture of branched and linear saturated C15-C19 alkanes and the ester of a fatty acid and dextrin are readily biodegradable according to OECD 301B.

The cosmetic composition may comprise also further organic or inorganic UV filters known to the person skilled in the art of cosmetics and sun protection.

The cosmetic composition typically comprises other ingredients which are suitable for the use in cosmetic compositions.

The cosmetic composition comprises preferably water.

The cosmetic compositions preferably may be in the form of a suspension or dispersion in solvents or fatty substances, or alternatively in the form of an emulsion or micro emulsion (in particular of oil-in-water (O/W-) or water-in-oil (W/O-)type, silicone-in-water (Si/W-) or water-in-silicone (W/Si-)type, PIT-emulsion, multiple emulsion (e.g. oil-in-water-in oil (O/W/O-) or water-in-oil-in-water (W/O/W-) type), pickering emulsion, hydrogel, alcoholic gel, lipogel, one- or multiphase solution or vesicular dispersion or other usual forms, which can also be applied by pens, as masks or as sprays.

Preferred cosmetic compositions in all embodiments of the present invention comprise water and are in the form of an emulsion.

The emulsion particularly contain an oily phase and an aqueous phase such as in particular O/W, W/O, Si/W, W/Si, O/W/O, W/O/W multiple or a pickering emulsions.

The total amount of the oily phase present in such emulsions is preferably at least 10 wt.-%, such as in the range from 10 to 60 wt.-%, preferably in the range from 15 to 50 wt.-%, most preferably in the range from 15 to 40 wt.-%, based on the total weight of the cosmetic composition.

The amount of the aqueous phase present in such emulsions is preferably at least 20 wt. %, such as in the range from 40 to 90 wt.-%, preferably in the range from 50 to 85 wt.-%, most preferably in the range from 60 to 85 wt.-%, based on the total weight of the cosmetic composition.

More preferably, the cosmetic compositions are in the form of an oil-in-water (O/W) emulsion comprising an oily phase dispersed in an aqueous phase in the presence of an O/W- respectively Si/W-emulsifier. The preparation of such emulsions is well known to a person skilled in the art.

The compositions in form of O/W emulsions can be provided, for example, in all the formulation forms for O/W emulsions, for example in the form of serum, milk or cream, and they are prepared according to the usual methods. The compositions are preferably intended for topical application and can in particular constitute a dermatological or cosmetic composition, for example intended for protecting human skin against the adverse effects of UV radiation (antiwrinkle, anti-ageing, moisturizing, sun protection and the like).

The cosmetic composition further preferably comprises at least one emulsifier, preferably an anionic emulsifier. Preferably the anionic emulsifier is an anionic emulsifier selected from the group consisting of potassium cetyl phosphate, disodium cetearyl sulfosuccinate, sodium stearoyl glutamate, sodium stearoyl lactylate, glyceryl stearate citrate and sodium cocoyl isethionate.

In one advantageous embodiment, the cosmetic compositions in addition contain a phosphate ester emulsifier. Among the preferred phosphate ester emulsifier are C8-10 Alkyl Ethyl Phosphate, C9-15 Alkyl Phosphate, Ceteareth-2 Phosphate, Ceteareth-5 Phosphate, Ceteth-8 Phosphate, Ceteth-10 Phosphate, Cetyl Phosphate, C6-10 Pareth-4 Phosphate, C12-15 Pareth-2 Phosphate, C12-Pareth-3 Phosphate, DEA-Ceteareth-2 Phosphate, DEA-Cetyl Phosphate, DEA-Oleth-3 Phosphate, Potassium cetyl phosphate, Deceth-4 Phosphate, Deceth-6 Phosphate and Trilaureth-4 Phosphate. A particular phosphate ester emulsifier is potassium cetyl phosphate e.g. commercially available as Amphisol® K at DSM Nutritional Products Ltd Kaiseraugst.

The cosmetic composition can also comprise nonionic emulsifiers.

Examples of nonionic emulsifier include condensation products of aliphatic (C8-C18) primary or secondary linear or branched chain alcohols with alkylene oxides, usually ethylene oxide and generally having from 6 to 30 ethylene oxide groups. Other representative nonionic emulsifiers include mono- or di-alkyl alkanolam ides such as e.g. coco mono- or di-ethanolamide and coco mono-iso-propanolamide. Further nonionic emulsifiers which can be included are the alkyl polyglycosides (APGs). Typically, the APG is one which comprises an alkyl group connected (optionally via a bridging group) to a block of one or more glycosyl groups such as e.g. Oramix™ NS 10 ex Seppic; PLANTACARE® 818UP, PLANTACARE® 1200 and PLANTACARE® 2000 ex BASF.

If the cosmetic composition is an O/W emulsion, then it preferably contains at least one O/W- or Si/W-emulsifier selected from the list of PEG-30 Dipolyhydroxystearate, PEG-4 Dilaurate, PEG-8 Dioleate, PEG-40 Sorbitan Peroleate, PEG-7 Glyceryl Cocoate, PEG-20 Almond Glycerides, PEG-25 Hydrogenated Castor Oil, Glyceryl Stearate (and) PEG-100 Stearate, PEG-7 Olivate, PEG-8 Oleate, PEG-8 Laurate, PEG-60 Almond Glycerides, PEG-20 Methyl Glucose Sesquistearate, PEG-40 Stearate, PEG-100 Stearate, PEG-80 Sorbitan Laurate, Steareth-2, Steareth-12, Oleth-2, Ceteth-2, Laureth-4, Oleth-10, Oleth-10/Polyoxyl 10 Oleyl Ether, Ceteth-10, Isosteareth-20, Ceteareth-20, Oleth-20, Steareth-20, Steareth-21, Ceteth-20, Isoceteth-20, Laureth-23, Steareth-100, glycerylstearatcitrate, glycerylstearate (self-emulsifying), stearic acid, salts of stearic acid, polyglyceryl-3-methylglycosedistearate. Further suitable emulsifiers are sorbitan oleate, sorbitan sesquioleate, sorbitan isostearate, sorbitan trioleate, Lauryl Glucoside, Decyl Glucoside, Sodium Stearoyl Glutamate, Sucrose Polystearate and Hydrated Polyisobuten.

Furthermore, one or more synthetic polymers may be used as an emulsifier. For example, PVP eicosene copolymer, acrylates/C10-30 alkyl acrylate crosspolymer, acrylates/steareth-20 methacrylate copolymer, PEG-22/dodecyl glycol copolymer, PEG-45/dodecyl glycol copolymer, and mixtures thereof.

Another particular suitable class of O/W emulsifiers are non-ionic self-emulsifying system derived from olive oil e.g. known as (INCI Name) cetearyl olivate and sorbitan olivate (Chemical Composition: sorbitan ester and cetearyl ester of olive oil fatty acids) sold under the tradename OLIVEM 1000.

Further suitable are commercially available polymeric emulsifiers such as hydrophobically modified polyacrylic acid such as Acrylates/C10-30 Alkyl Acrylate Crosspolymers which are commercially available under the tradename Pemulen® TR-1 and TR-2 by Noveon.

Another class of particularly suitable emulsifiers are polyglycerol esters or diesters of fatty acids also called polyglyceryl ester/diester (i.e. a polymer in which fatty acid(s) is/are bound by esterification with polyglycerine), such as e.g. commercially available at Evonik as Isolan GPS [INCI Name Polyglyceryl-4 Diisostearate/Polyhydroxystearate/Sebacate (i.e. diester of a mixture of isostearic, polyhydroxystearic and sebacic acids with Polyglycerin-4)] or Dehymuls PGPH available at Cognis (INCI Polyglyceryl-2 Dipolyhydroxystearate).

Also suitable are polyalkylenglycolether such as Brij 72 (Polyoxyethylen-(2)stearylether) or Brij 721 (Polyoxyethylene (21) Stearyl Ether e.g. available at Croda.

The at least one O/W respectively Si/W emulsifier is preferably used in an amount of 0.5 to 10 wt. % such as in particular in the range of 0.5 to 5 wt.-% such as most in particular in the range of 0.5 to 4 wt.-% based on the total weight of the composition.

Suitable W/O- or W/Si-emulsifiers are polyglyceryl-2-dipolyhydroxystearat, PEG-30 dipolyhydroxystearat, cetyl dimethicone copolyol, polyglyceryl-3 diiso-polyglycerol esters of oleic/isostearic acid, polyglyceryl-6 hexaricinolate, polyglyceryl-4-oleate, polygylceryl-4 oleate/PEG-8 propylene glycol cocoate, magnesium stearate, sodium stearate, potassium laurate, potassium ricinoleate, sodium cocoate, sodium tallowate, potassium castorate, sodium oleate, and mixtures thereof. Further suitable W/Si-emulsifiers are Lauryl Polyglyceryl-3 Polydimethylsiloxyethyl Dimethicone and/or PEG-9 Polydimethylsiloxyethyl Dimethicone and/or Cetyl PEG/PPG-10/1 Dimethicone and/or PEG-12 Dimethicone Crosspolymer and/or PEG/PPG-18/18 Dimethicone. The at least one W/O emulsifier is preferably used in an amount of about 0.001 to 10 wt.-%, more preferably in an amount of 0.2 to 7 wt.-% with respect to the total weigh of the composition.

The cosmetic compositions according preferably furthermore advantageously contain at least one co-surfactant such as e.g. selected from the group of mono- and diglycerides and/or fatty alcohols. The co-surfactant is generally used in an amount selected in the range of 0.1 to 10 wt.-%, such as in particular in the range of 0.5 to 6 wt.-%, such as most in particular in the range of 1 to 5 wt.-%, based on the total weight of the composition. Particular suitable co-surfactants are selected from the list of alkyl alcohols such as cetyl alcohol (Lorol C16, Lanette 16), ceteary1 alcohol (Lanette 0), stearyl alcohol (Lanette 18), behenyl alcohol (Lanette 22), glyceryl stearate, glyceryl myristate (Estol 3650), hydrogenated coco-glycerides (Lipocire Na10) as well as mixtures thereof.

The amount of emulsifier is preferably in the range between 0.1-6.0% by weight, more preferably between 0.25-5.0% by weight, particularly between 0.5-4.0% by weight, based on the total weight of the cosmetic composition.

The composition is preferably sulfate-free.

Hence, the cosmetic composition is preferably particularly free of sulfates of the group consisting of alkyl sulfates, alkyl ether sulfates, alkyl amido ether sulfates, alkylaryl polyether sulfates and monoglycerides sulfate as well as mixtures thereof.

The term "free" as used in the present document, for example in "sulfate-free", is used to mean that the respective substance is only present at amounts of less than 0.5% by weight, particularly less than 0.1% by weight, more particularly below 0.05% by weight, relative to the weight of the composition. Preferably, "free" means that the respective substance is completely absent in the composition.

The term "sulfate-free" is used in the present document to mean that the composition is free of any anionic tenside having a terminal anionic group of the formula

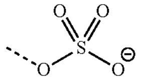.

The cosmetic composition is preferably free of cationic emulsifiers. Typical example for such cationic emulsifiers are isostearamidopropyl dimethylamine, stearalkonium chloride, stearamidoethyl diethylamine, behentrimonium methosulfate, behenoyl PG-trimonium chloride, cetrimonium bromide, behenamidopropyl dimethylamine behenate, brassicamidopropyl dimethylamine, stearamidopropyl dimethylamine stearate, cocamidopropyl PG-dimonium chloride, distearoylethyl hydroxyethylmonium methosulfate, dicocoylethyl hydroxyethylmonium methosulfate, distearoylethyl dimonium chloride, shea butteramidopropyltrimonium chloride, behenamidopropyl dimethylamine, brassicyl isoleucinate esylate, acrylamidopropyltrimonium chloride/acrylates copolymer, linoleamidopropyl ethyldimonium ethosulfate, dimethyl lauramine isostearate, isostearamidopropyl laurylacetodimonium chloride, particularly behentrimonium chloride, distearyldimonium chloride, cetrimonium chloride, steartrimonium chloride, and palmitamido-propyltrimonium chloride.

The composition may comprise preferably a further UV filter. The further UV filter may be solid or liquid. It is preferred that the further UV filter is a solid UV filter.

Suitable liquid organic UV-filter absorb light in the UV(B) and/or UV(A) range and are liquid at ambient temperature (i.e. 25° C.). Such liquid UV-filter are well known to a person in the art and encompass in particular cinnamates such as e.g. octyl methoxycinnamate (PARSOL® MCX) and isoamyl methoxycinnamate (Neo Heliopan® E 1000), salicylates such as e.g. homosalate (3,3,5 trimethyl-cyclohexyl 2-hydroxybenzoate, PARSOL® HMS) and ethylhexyl salicylate (also known as ethylhexyl salicylate, 2-ethylhexyl 2-hydroxybenzoate, PARSOL® EHS), acrylates such as e.g. octocrylene (2-ethylhexyl-2-cyano-3,3-diphenylacrylate, PARSOL® 340) and ethyl 2-cyano-3,3 diphenylacrylate, esters of benzalmalonic acid such as in particular dialkyl benzalmalonates such as e.g. di (2-ethylhexyl) 4-methoxybenzalmalonate and polysilicone 15 (PARSOL® SLX), dialkylester of naphthalates such as e.g. diethylhexyl 2,6-naphthalate (Corapan® TQ), syringylidene malonates such as e.g. diethylhexyl syringylidene malonate (Oxynex® ST liquid) as well as benzotriazolyl dodecyl p-cresol (Tinoguard® TL) as well as benzophenone-3 and drometrizole trisiloxane.

Particular advantageous liquid organic UV-filter are octyl methoxycinnamate, homosalate, ethylhexyl salicylate, octocrylene, diethylhexyl 2,6-naphthalate, diethylhexyl syringylidene malonate, benzotriazolyl dodecyl p-cresol, benzo-phenone-3, drometrizole trisiloxane as well as mixtures thereof.

In a preferred embodiment, the liquid UV filter is a liquid UV(B) filter which is selected from the group consisting of ethylhexyl methoxycinnamate, octocrylene, homosalate, ethylhexyl salicylate, benzophenone-3 and drometrizole trisiloxane.

Suitable solid organic UV-filter absorb light in the UV(B) and/or UV(A) range and are solid at ambient temperature (i.e. 25° C.). Particularly suited solid UV-filters are of the group consisting of bis-ethylhexyloxyphenol methoxyphenyl triazine, butyl methoxydibenzoyl methane, methylene bis-benzotriazolyl tetramethylbutylphenol, diethylamino hydroxybenzoyl hexyl benzoate, ethylhexyl triazone, 4-methylbenzylidene camphor and 1,4-di(benzoxazol-2'-yl) benzene.

A preferred solid organic UV(A) filter is a UV(A) filter which is selected from the group consisting of bis-ethylhexyloxyphenol methoxyphenyl triazine, butyl methoxydibenzoyl methane, methylene bis-benzotriazolyl tetramethylbutylphenol, diethylamino hydroxybenzoyl hexyl benzoate and tris-biphenyl triazine.

A preferred solid organic UV(B) filter is a UV(B) filter which is selected from the group consisting of ethylhexyl triazone (=Uvinul® T150), and 4-methylbenzylidene camphor (=PARSOL® 5000).

The total amount of organic UV filter (s) depends strongly on the targeted UV protection.

It is preferred that the amount of a solid organic UV filter, particular of solid organic UV(A) filter, is selected in the range of 0.1 to about 6 wt.-%, preferable in the range of 0.5 to 5 wt.-%, most preferably in the range of 1 to 4 wt.-%.

It is further preferred that amount of a solid organic UV filter, particular of solid organic UV(B) filter, is selected in the range of 0.1 to about 6 wt.-%, preferable in the range of 0.5 to 5 wt.-%, most preferably in the range of 1 to 4 wt.-%.

It is even further preferred that amount of a liquid organic UV filter, particular of liquid organic UV(B) filter, is selected in the range of 0.1 to about 10 wt.-%, preferable in the range of 0.5 to 12 wt.-%, most preferably in the range of 1 to 10 wt.-%.

The cosmetic composition further may comprise cosmetic carriers, excipients and diluents as well as additives and active ingredients commonly used in the skin care industry which are suitable for use in the cosmetic compositions are for example described in the International Cosmetic Ingredient Dictionary & Handbook by Personal Care Product Council (http://www.personalcarecouncil.org/), accessible by the online INFO BASE (http://online.personalcarecouncil.org/jsp/Home.jsp), without being limited thereto.

Such possible ingredients of the cosmetic composition are particularly enhance the performance and/or consumer acceptability such as preservatives, antioxidants, fatty substances/oils, thickeners, softeners, light-screening agents, moisturizers, fragrances, co-surfactants, fillers, sequestering agents, cationic-, nonionic- or amphoteric polymers or mixtures thereof, acidifying or basifying agents, viscosity modifiers, and natural hair nutrients such as botanicals, fruit extracts, sugar derivatives and/or amino acids or any other ingredients usually formulated into cosmetic compositions. The necessary amounts of the adjuvants and additives can, based on the desired product, easily be chosen by a person skilled in the art in this field and will be illustrated in the examples, without being limited hereto.

Particularly suitable thickeners in all embodiments are xanthan gum, gellan gum and/or carboxymethylcellulose. Most preferably in all embodiments the thickener is xanthan gum or gellan gum.

Such thickener(s) are preferably used in an amount (total) selected in the range from 0.1 to 1 wt.-%, more preferably in an amount of 0.1 to 0.5 wt.-%, based on the total weight of the cosmetic composition.

The cosmetic compositions have preferably a pH in the range from 3 to 10, preferably a pH in the range from 4 to 8 and most preferably a pH in the range from 4 to 7.5. The pH can easily be adjusted as desired with suitable acids such as e.g. citric acid or bases such as NaOH according to standard methods in the art.

The cosmetic composition is preferably sulfate-free and/or free of para-bens, and/or silicone oils and/or silicone surfactants.

The cosmetic composition is preferably a topical composition.

The term "topical" as used herein is understood here to mean external application to keratinous substances, which are in particular the skin, scalp, eyelashes, eyebrows, nails, mucous membranes and hair, preferably the skin.

As the topical compositions are intended for topical application, it is well understood that they comprise a physiologically acceptable medium, i.e. a medium compatible with keratinous substances, such as the skin, mucous membranes, and keratinous fibers. In particular, the physiologically acceptable medium is a cosmetically acceptable carrier.

The term "cosmetically acceptable carrier" refers to all carriers and/or excipients and/or diluents conventionally used in cosmetic compositions such as in particular in sun care products.

Preferably the cosmetic composition is a skin care preparation, decorative preparation, or a functional preparation.

Examples of skin care preparations are, in particular, light protective preparations, anti-ageing preparations, preparations for the treatment of photo-ageing, body oils, body lotions, body gels, treatment creams, skin protection ointments, skin powders, moisturizing gels, moisturizing sprays, face and/or body moisturizers, skin-tanning preparations (i.e. compositions for the artificial/sunless tanning and/or browning of human skin), for example self-tanning creams as well as skin lightening preparations.

Examples of functional preparations are cosmetic or pharmaceutical compositions containing active ingredients such as hormone preparations, vitamin preparations, vegetable extract preparations and/or anti-ageing preparations without being limited thereto.

The cosmetic composition is preferably a skin care composition.

In a most preferred embodiment, the cosmetic composition is a sun care composition. Sun care compositions are light-protective preparations (sun care products), such as sun protection milks, sun protection lotions, sun protection creams, sun protection oils, sun blocks or day care creams with a SPF (sun protection factor). Of particular interest are sun protection creams, sun protection lotions, sun protection milks and sun protection preparations.

The cosmetic compositions have improved sensory properties, particular improved afterfeel, and are capable to have a higher amount of UV-filter of the formula (I) been solubilized as compared with the respective cosmetic compositions being devoid of said ester of a fatty acid and dextrin and devoid of mixture of branched and linear saturated C15-C19 alkanes and particularly devoid of any silicone oil.

It has been observed that UV filter of formula (I) can be better solubilized in liquid saturated C8-C30 alkanes by adding an ester of a fatty acid and dextrin.

As both ingredients are available from biological origin, it is possible to obtain this improvement in a sustainable way which is a big advantage of the present invention.

Hence, in a further aspect, the present invention relates to the use of adding an ester of a fatty acid and dextrin to increase the solubilization of solid organic UV filters in liquid saturated C8-C30 alkanes, particularly in branched and linear saturated C15-C19 alkanes.

The liquid saturated C8-C30 alkanes are particularly selected from the group consisting of C8-C30 mineral oils, decane, undecane, dodecane, hexadecane, octadecane, squalene (=2,6,10,15,19,23-hexamethyltetracosane), farnesane (=2,6,10-trimethyldodecane), dodecane, isopentadecane, isohexadecane, isooctadecane, isononadecane, and the branched and linear saturated C15-C19 alkanes, particularly the in branched and linear saturated C15-C19 alkanes as discussed above in great details.

It has been observed that the UV filter of formula (I) can be better solubilized in a cosmetic composition by combining the UV filter of formula (I) with particularly an ester of a fatty acid and dextrin and a mixture of branched and linear saturated C15-C19 alkanes.

Hence, in a further aspect, the present invention relates to a method of increasing the solubilization of a UV filter of formula (I) in a cosmetic composition by combining the UV filter of formula (I)

(I)

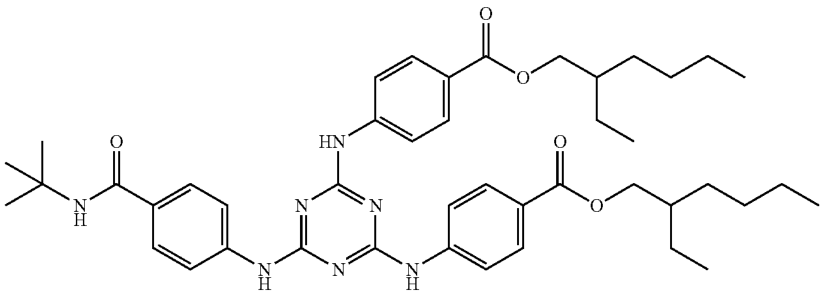

with an ester of a fatty acid and dextrin and a mixture of branched and linear saturated C15-C19 alkanes.

EXAMPLES

The present invention is further illustrated by the following experiments.

Cosmetic Compositions and Solubilisation of Iscotrizinol

Preparation of a Premix

In examples 1 and 2, the dextrin palmitate has been premixed with a part of the C15-C19 alkane to form a pre-mix (Dextrin palmitate 25% by weight).

Said premix has then mixed with the UV filter and the rest of the C15-19 alkane by a magnetic stirrer at 80 C, let cool down without any stirring to 25° C. After one week storage of the solution at 25° C. a sample has been taken with a pipette from the bottom of the flask and observed under the microscope (Microscope Zeiss AX-under polarizer light, magnification×100, camera Deltapix Invenio 5D). The microscopic pictures are shown in the FIGS. 1 to 4.

The viscosities have been measured on a Rheometer AR550 from TA Instruments using a 40 mm plate and a shear 10/s at 25° C.

TABLE 1

Cosmetic compositions comprising Iscotrizinol (all ingredients in % by weight).

Figure 2:
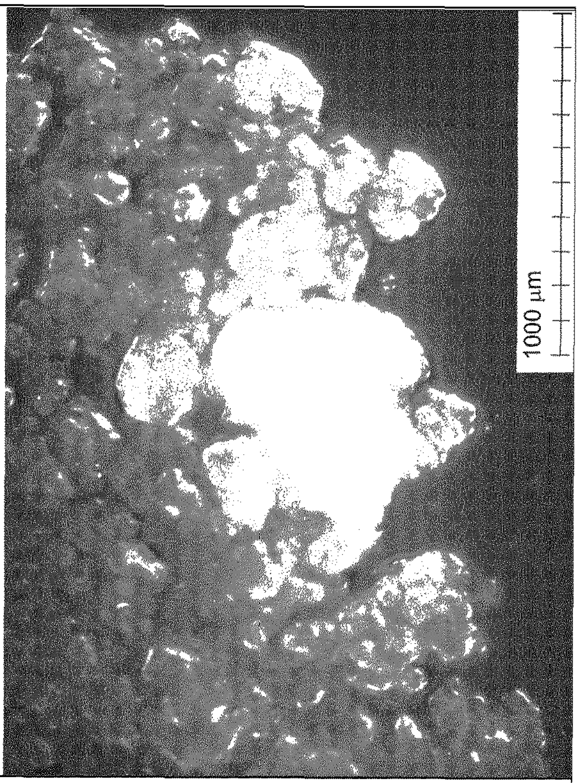
Figure 3:
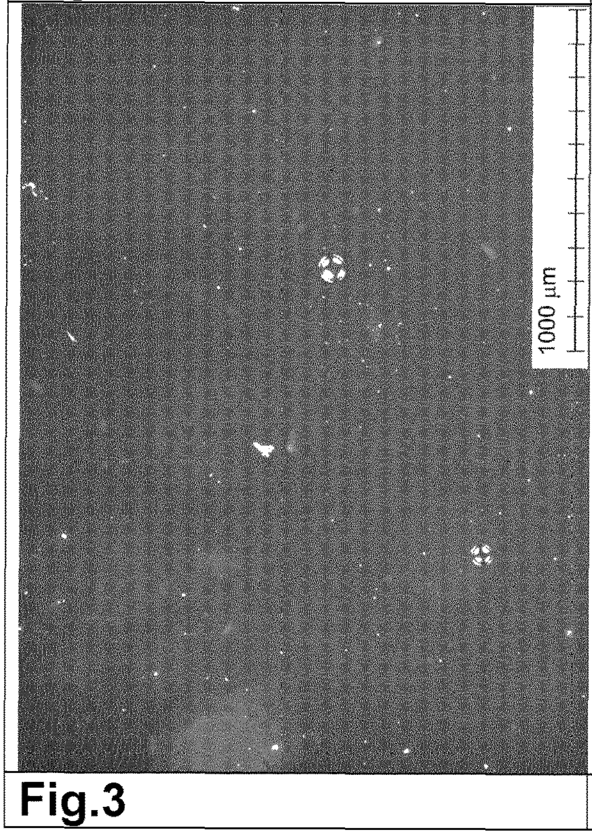
Figure 4:
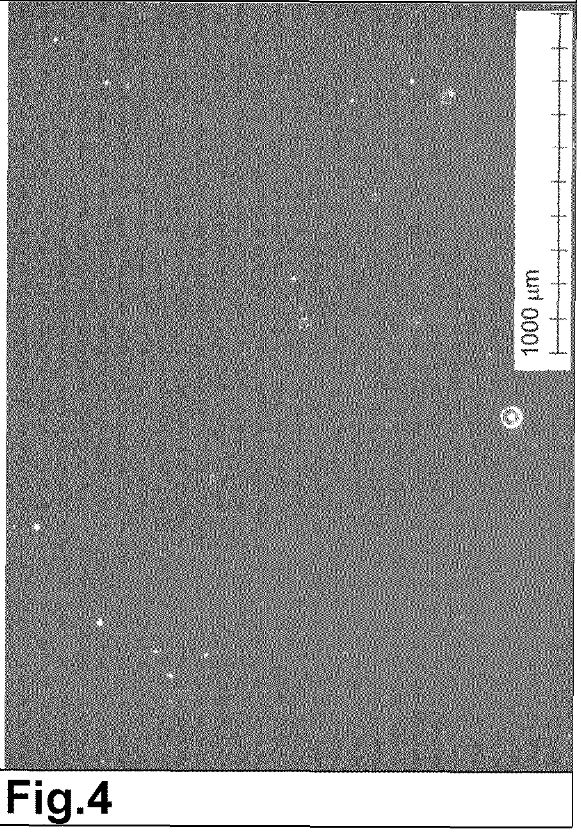

| | Ref. 1 | 1 | 2 | Ref. 2 |
|---|---|---|---|---|
| UVASORB ® HEB [%][1] | 2 | 2 | 2 | 2 |
| C15-19 alkane [%][2] | 98 | 88 | 88 | 88 |
| Dextrin Palmitate 1 [%][3] | | 10 | | |
| Dextrin Palmitate 2 [%][4] | | | 10 | |
| Oilkemia 5S [%][5] | | | | 10 |
| Aspect | Clear with many crystals | White gel with very few crystals | White gel with very few crystals | No gel with many crystals and agglomerate |
| Viscosity [mPa · s] | <10 | 37'460 | 3'023 | <10 |
| Microscope picture | FIG. 1 | FIG. 3 | FIG. 4 | FIG. 2 |

[1]Iscotrizinol

[2]EMOGREEN ™ L19

[3]Rheopearl ® KL2, Chiba Flour Milling

Dextrin Palmitate: $M_n$ = 11'300-11'500 Da, determined by SEC/GPC

[5]Polyurethane polymer (INCI Polyuethane-79) (30% in Caprylic/Capric triglycerides), Lubrizol It has been shown, that the UV filter was not been able to solubilize in C15-19 alone (Ref.1) or in a polyurethane-based thickener (Ref.2). In both cases significant amounts of crystals (and agglomerates in Ref.2) of the UV filter have been found at the bottom off the flask (see FIG. 1, 2). In both cases, no gel was formed and the viscosity of the composition was very low (<10 mPa·s).

In case of the examples 1 and 2 the UV filter was excellently solubilized and only a few crystals (see FIGS. 3 and 4), have been observed. Example 2 showed less crystals than example 1. In both cases, a gel has formed and a viscosity of more than 2000 mPa·s has been observed.

The invention claimed is:

1. A composition comprising:

an ester of a fatty acid and dextrin;

a mixture of branched and linear saturated C15-C19 alkanes; and a UV-filter of the formula (I):

(I)

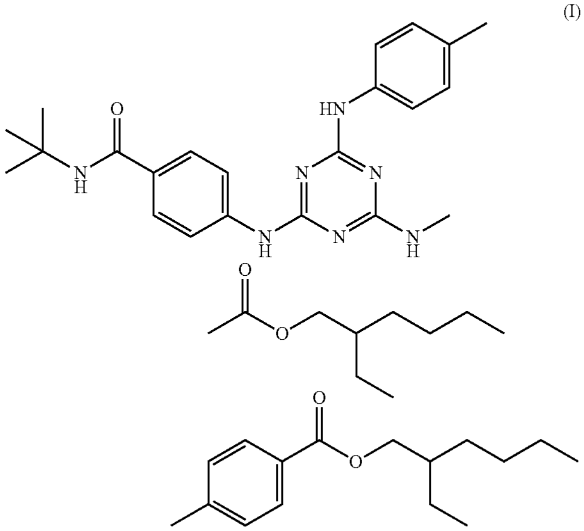

wherein the amount of branched saturated C15-C19 alkanes in the mixture of branched and linear saturated C15-C19 alkanes is more than 80% by weight.

2. The composition according to claim 1, wherein the amount of linear saturated C15-C19 alkanes in the mixture of branched and linear saturated C15-C19 alkanes is less than 10% by weight.

3. The composition according to claim 1, wherein amount of branched saturated C18 alkane is more than 50% by weight, relative to the weight of the mixture of branched and linear saturated C15-C19 alkanes.

4. The composition according to claim 1, wherein the fatty acid of the ester of a fatty acid and dextrin is a C14-C18 fatty acid.

5. The composition according to claim 1, wherein the dextrin of the ester of a fatty acid and dextrin has an average degree of glycopolymerization of between 3 and 20.

6. The composition according to claim 1, wherein the ester of a fatty acid and dextrin has an average number of esterified hydroxyl groups of more than 3 per glucose unit.

7. The composition according to claim 1, wherein the ester of a fatty acid and dextrin has a molecular weight Mn of between 8,000 and 16,000 Da.

8. The composition according to claim 1, wherein the ratio of the weight of the ester of a fatty acid and dextrin to the weight of the mixture of branched and linear saturated C15-C19 alkanes is less than 100% by weight.

9. The composition according to claim 1, wherein the weight ratio of the UV-filter of the formula (I) to the ester of a fatty acid and dextrin is 100:1 to 1:100.

10. The composition according to claim 1, wherein the composition comprises water and is in the form of an emulsion.

11. The composition according to claim 1, wherein the composition is in the form of a gel.

12. The composition according to claim 1, wherein the composition has a Sun Protection Factor (SPF) of 10 or higher.

13. A method of increasing the solubilization of a UV filter of formula (I) in a cosmetic composition which comprises combining the UV filter of formula (I):

(I)

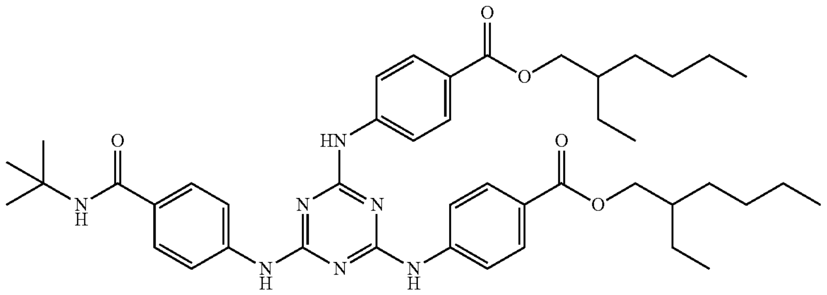

with an ester of a fatty acid and dextrin and a mixture of branched and linear saturated C15-C19 alkanes.

14. The composition according to claim 2, wherein the amount of linear saturated C15-C19 alkanes in the mixture of branched and linear saturated C15-C19 alkanes is more than 5% by weight.

15. The composition according to claim 3, wherein the amount of branched saturated C18 alkane is more than 70% by weight, relative to the weight of the mixture of branched and linear saturated C15-C19 alkanes.

16. The composition according to claim 4, wherein the fatty acid of the ester of a fatty acid and dextrin is a linear C14-C18 fatty acid.

17. The composition according to claim 4, wherein the fatty acid of the ester of a fatty acid and dextrin is palmitic acid.

18. The composition according to claim 8, wherein the ratio of the weight of the ester of a fatty acid and dextrin to the weight of the mixture of branched and linear saturated C15-C19 alkanes is in the range of 50-80% by weight.

19. The composition according to claim 18, wherein the weight ratio of the UV-filter of the formula (I) to the ester of a fatty acid and dextrin is 10:1 to 1:10.

* * * * *